(12) United States Patent
Combette et al.

(10) Patent No.: US 8,192,980 B2
(45) Date of Patent: Jun. 5, 2012

(54) MICROREACTOR, PROCESS FOR THE PREPARATION THEREOF, AND PROCESS FOR CARRYING OUT A BIOCHEMICAL OR BIOLOGICAL REACTION

(75) Inventors: Philippe Combette, Castelnau-le-Lez (FR); Olivier Constantin, Grenoble (FR); Françoise Vinet, Grenoble (FR); Gilles Marchand, Pierre Chatel (FR)

(73) Assignee: Commissariat a l'Energie Atomique, Paris (FR)

( * ) Notice: Subject to any disclaimer, the term of this patent is extended or adjusted under 35 U.S.C. 154(b) by 996 days.

(21) Appl. No.: 10/514,066

(22) PCT Filed: May 16, 2003

(86) PCT No.: PCT/FR03/01492
§ 371 (c)(1),
(2), (4) Date: Sep. 2, 2005

(87) PCT Pub. No.: WO03/097229
PCT Pub. Date: Nov. 27, 2003

(65) Prior Publication Data
US 2006/0051858 A1 Mar. 9, 2006

(30) Foreign Application Priority Data
May 17, 2002 (FR) .................................. 02 06084

(51) Int. Cl.
*C12M 1/34* (2006.01)
*C12M 3/00* (2006.01)
(52) U.S. Cl. ............... 435/288.5; 435/299.1; 435/305.2; 422/551; 422/552; 422/130

(58) Field of Classification Search ............... 435/288.5, 435/288.6, 6, 287.1
See application file for complete search history.

(56) References Cited

U.S. PATENT DOCUMENTS

| 5,030,352 | A | * | 7/1991 | Varady et al. ............... 210/502.1 |
| 6,156,273 | A | * | 12/2000 | Regnier et al. .................. 422/70 |
| 6,368,871 | B1 | * | 4/2002 | Christel et al. ................ 436/180 |
| 7,485,454 | B1 | * | 2/2009 | Jury et al. .................. 435/288.5 |
| 2003/0148401 | A1 | * | 8/2003 | Agrawal et al. ................ 435/7.9 |

FOREIGN PATENT DOCUMENTS
WO   WO-93/22053   11/1993
WO   WO-99/09042   2/1999

OTHER PUBLICATIONS

Pereira, Gha, et al. "Multi-point immobilization of Penicillin G Acylase on Silica-Glyoxyl: influence of the degree of activation" 1997, Braz. J. Chem. Eng. vol. 14, No. 4.*

(Continued)

*Primary Examiner* — William H Beisner
*Assistant Examiner* — Danielle Henkel
(74) *Attorney, Agent, or Firm* — Brinks Hofer Gilson & Lione

(57) ABSTRACT

A microreactor is shown having an inlet or feed channel, an inlet or feed zone for a flow of fluid, a reaction zone, an outlet zone and an outlet or evacuation channel, the zones and channels being in fluid communication, and at least one compound such as an enzyme capable of producing a biological or biochemical reaction with at least one constituent of the flow of fluid, the compound being attached to the surfaces of the inlet zone, reaction zone, and outlet zone.

39 Claims, 5 Drawing Sheets

OTHER PUBLICATIONS

Dickey, Cynthia K., et al.,"Enzyme Catalyzed Biochemical Production in a Polydimethylsiloxane Microreactor",*Proc. SPIE-Int. Soc. Opt. Eng.* (2000), 4177 (Microfluidic Devices and Systems III) pp. 56-64.

Fletcher, Paul D., et al.,"Theoretical Considerations of Chemical Reactions in Micro-Reactors Operating Under Electroosmotic and Electrophoretic Control",*Analyst*, 124:1273-1282 (1999).

He, Bing, et al.,"A Picoliter-Volume Mixer for Microfluidic Analytical Systems",*Analytical Chemistry*, 2000.

He, Bing, et al.,"Capillary Electrochromatography of Peptides in a Microfabricated System", *Journal of Chromatography A*, vol. 853, No. 1-2, pp. 257-262 (1999).

He, B., et al.,"Fabrication of Nanocolumns for Liquid Chromatography",*Anal. Chem.* 70(18):3790-7 (1998).

He, Bing, et al.,"Microfabricated Filters for Microfluidic Analytical Systems",*Analytical Chemistry*, 71(7):1464-1468 (1999).

McCreedy, Tom,"Rapid Prototyping of Glass and PDMS Microstructures for Micro Total Analytical Systems and Micro Chemical Reactors by Microfabrication in the General Laboratory",*Analytica Chimica Acta* 427:39-43 (2001).

Miyazaki, M., et al.,"Chemical Abstracts 2001:335569",*Chem. Lett* (2001), (5), 442-446.

Slentz, B.E., et al.,"Capillary Electrochromatography of Peptides on Microfabricated Poly(dimethylsiloxane) Chips Modified by Cerium(IV)-catalyzed Polymerization",*J. Chromatogr. A.*, 948(1-2):225-33 (2002).

Xiong, Li, et al.,"Channel-specific Coatings on Microfabricated Chips", *Journal of Chromatography A*, vol. 924, No. 1-2, pp. 165-176 (2001).

* cited by examiner

MICROREACTOR, PROCESS FOR THE PREPARATION THEREOF, AND PROCESS FOR CARRYING OUT A BIOCHEMICAL OR BIOLOGICAL REACTION

The present invention relates to a microreactor.

The invention also relates to a process for preparing or manufacturing such a microreactor.

Finally, the invention relates to a process for carrying out a biochemical or biological reaction which uses said microreactor.

The field of the invention can be defined as that of miniaturized systems of Microsystems which are used essentially for chemical analysis and synthesis.

The favourite fields for chemical microreactors are liquid- and gas-phase reactions, including homogeneous and heterogeneous catalysis, catalytic oxidation, heterocyclic synthesis and photochemical reactions.

In particular, these processes have shown the advantage in using microreactor technology for chemistry in solution and biological bioapplications.

Examples of analytical Microsystems or microreactors for synthesis are more specifically described in documents [1] to [9].

In particular, document [3] concerns the production of nanocolumns for liquid chromatography by micromachining techniques.

The microcolumns comprise "monoliths", preferably hexagonal monoliths, supporting the stationary phase, and possess inlet and outlet channels having a specific architecture with a network of channels, which means that the flow of liquid going into the column is divided in two, repeatedly, before it reaches the top of the column.

The total number of channels (C) of the chromatographic column, per se, which can be fed is for example $C=2^n$, where n is the number of times the liquid flow is divided.

The stationary phase consists of electrostatically bonded poly(styrene sulphate).

The poly(styrene sulphate) is absorbed, from a solution, onto the surface of the channels after silylation of the walls of the channels using (gamma-aminopropyl)trimethoxysilane.

Like document [3], U.S. Pat. No. 6,156,273 describes a column for separation by chromatography, electrochromatography and electrophoresis, which comprises multiple colocated monolith support structures, which define interconnected channels.

The surfaces of the monoliths can be treated so as to provide interactions between these surfaces and a sample which crosses the separation column, in order to perform a separation of the constituents of the sample.

Among the coatings with which the monoliths can be provided, mention may be made, for example, of antibody coatings, cationic or anionic coatings, chelating-agents, organic coatings, such as complex sugars and heparin, gels and reverse-phase coatings, such as C18.

In that document, no reaction takes place in the column, and no new product originating from the reaction of the coating which is on the surfaces of the monoliths with the constituents of the treated sample is generated.

That document provides a simple common chromatographic process with more or less substantial retention of the various constituents of the sample crossing the column, as a function of their affinity for the coating.

In document [9], since the enzyme and the product to be treated, to be digested, react in liquid phase, in solution, in the mass of the fluid, the drawbacks of operating in such a way (compared to the invention, where the enzyme is attached to the wall) are as follows: parasitic reactions such as, for example, autolysis in the case of a digestive enzyme and, consequently, limiting of the concentrations.

The digestion rate can be optimized by confining the digestion reactions in smaller volumes. The volumes available in integrated devices on chips make it possible to use very small amounts of samples, in very small reaction zones, in order to increase the digestion rates. It has recently been shown that it is possible to digest proteins inside wells produced in microdevices. As has already been seen, the digestion being carried out in solution results in autodigestion of the proteins, which can interfere with an analysis by mass spectrometry. This phenomenon is all the more important when it is desired to improve the rate of digestion by increasing the concentrations of proteolytic species.

The use of functionalized beads makes it possible to considerably reduce this autolysis, also increases the stability of the enzyme, and provides higher digestion rates since the amount of digestive enzyme can be considerably increased.

However, the operation of filling the microchannels with functional beads remains a delicate and relatively unreliable operation.

It emerges from the above text that there is a need for a microreactor which makes it possible to carry out chemical and/or biological reactions with a very high yield, with a small amount of reactant, such as an enzyme, and at a rate that is also high.

For example, in the case of enzymatic digestion, there is a need for a microreactor which, while limiting the problems of autolysis, provides high rates and is reliable and easy to use, unlike the microreactors using functionalized beads.

The aim of the present invention is therefore to provide a microreactor which satisfies, inter alia, these needs.

The aim of the present invention is also to provide a microreactor which does not have the drawbacks, limitations, faults and disadvantages of the microreactors of the prior art.

This aim, and even others, are achieved in accordance with the invention by means of a microreactor comprising an inlet or feed channel, an inlet or feed zone for a flow of fluid, an active zone comprising means which confer on it a high surface-to-volume ratio, an outlet zone and an outlet or evacuation channel, said zones and channels being in fluid communication, characterized in that the active zone is a reaction zone comprising at least one compound capable of producing a biological or biochemical reaction with at least one constituent of said flow of fluid, said compound being attached to the surfaces of said reaction zone.

Advantageously, in the microreactor according to the invention:

said inlet zone comprises means for giving said flow of fluid a constant flow rate, for evenly distributing the flow of fluid over the entire cross section of said reaction zone, and for increasing the surface/volume ratio as the flow of fluid progresses towards the active zone which is a reaction zone;

said at least one compound capable of producing a biological or biochemical reaction with at least one constituent of said flow of fluid is attached to the surfaces of said inlet zones, active zone which is a reaction zone, and outlet zone;

said outlet zone comprises means for regrouping the flow of fluid derived from the active zone which is a reaction zone comprising the products derived from said biological or biochemical reaction, and for reducing the surface-to-volume ratio as the flow of fluid progresses from the active zone which is a reaction zone towards said outlet channel, and for evacuating said flow of fluid.

It is clear that the flow of fluid, when it flows in the device of the invention, encounters successively the inlet zone, then the active zone (reaction zone) and, finally, the outlet zone, then the outlet channel.

The microreactor according to the invention differs, first of all, fundamentally from the device described for example in U.S. Pat. No. 6,156,273, which is fundamentally a separation device that obeys the conventional rules of chromatography and not a device aimed at carrying out a reaction, i.e. a reactor.

In this document U.S. Pat. No. 6,156,273, compounds are attached to the walls of the device, but their aim is to retain to a greater or lesser degree the various constituents of the liquid sample which crosses the device.

This is a typical retention phenomenon in chromatography, the aim of which is to prolong by varying amounts the period of time that the constituents of the treated liquid spend in the column, in order to ensure the staggered exit, and therefore the separation, thereof.

The constituents of the treated liquid undergo no conversion in the column and no new product is generated inside the column. In fact, in the device of the prior art, the zone which can be defined as an active zone makes it possible to perform chromatography, with no reaction, whereas in the device according to the invention, the active zone is a reaction zone since attached therein are compounds capable of producing a reaction.

On the contrary, the invention relates not to a separation device, but to a reactor, which means that the compounds attached to the surfaces of the various zones of the device, namely of the microreactor, according to the invention, produce a biological or biochemical reaction with at least one constituent of the flow of fluid, that this constituent is converted and that new products are created and then collected.

In other words, in the reactor according to the invention, a sample which circulates in the reactor will, according to the invention, interact with the compounds capable of reacting, that are attached to the surfaces of the reactor, and thus create products derived from this reaction, unlike, again, the device according to document U.S. Pat. No. 6,156,273, where the compounds, the coating, attached to the walls simply promote the more or less prolonged attachment of the constituents of the sample, but do not generate new products.

The device according to the invention is also fundamentally different from the devices described in particular in document [9], in which devices the reaction between the compound capable of producing a biological or biochemical reaction and at least one constituent of the flow of fluid occurs in the liquid phase, in solution, said compound being absolutely not immobilized, attached to the surfaces of the device, as in the microreactor according to the invention.

By virtue of this essential characteristic of the microreactor according to the invention, the concentrations of the species immobilized on the surface can be largely increased without the appearance of parasitic reactions such as, for example, autolysis in the case of a digestive enzyme.

Finally, compared to the microreactors comprising a filling of microbeads, the microreactor according to the invention has the advantage of being more reliable and simpler to prepare and of having, likewise, a reliable and simple mode of functioning.

The device according to the invention is described as microreactor; this name is commonly used in this field of the art and is perfectly clear to those skilled in the art. However, it could be useful to specify that the largest dimension of the microreactor according to the invention, which is for example its length or height, is generally from 10 mm to 30 mm.

Of course, the applications and/or the nature of the products used may require different dimensions.

The compound capable of producing a biological or biochemical reaction may be any compound that corresponds to such a definition, but it is generally chosen from enzymes.

In other words, it may be any compound capable of interacting with a constituent, or target molecule, present in the flow of fluid which crosses the microreactor, and of converting said constituent by means of a molecular biology reaction so as to obtain, from this constituent, a new product. It may involve, for example, an interaction and reaction of the enzyme/substrate type, where said compound is an enzyme and said constituent is a substrate for said enzyme.

Those skilled in the art will find numerous other obvious applications of the present invention based on this definition.

According to the invention, when this compound is an enzyme, it may be chosen from the oxidoreductase class, the transferase class, the hydrolase class, the lyase class, the isomerase class, or the ligase or synthetase class.

It may for example be an enzyme with lytic activity, such as a protease, a nuclease, a lipase, a glycolase, a kinase, etc.; an enzyme having an activity that modifies or acts on nucleic acids, such as DNA or RNA polymerase, primase, DNA ligase, a nuclease, a reverse transcriptase, a kinase, a phosphatase, a phosphorylase, a restriction endonuclease, a topoisomerase, a transferase, etc.

Among proteases, mention may be made, for example, of endopeptidases such as pepsin, trypsin, chymotrypsin, cathepsins A, B and C; and exopeptidases such as carbopeptidases, aminopeptidases and dipeptidases.

Preferably, the enzyme is trypsin and the substrate is a peptide or a protein.

According to the present invention, when the compound which is capable of interacting with the constituent of the fluid is an enzyme, the microreactor can be called an enzyme microreactor. For example, when the enzyme is trypsin, it may be called a tryptic microreactor; or else, for example when the enzyme is a polymerase, it may be called a polymerase microreactor.

The compound capable of producing a biological or biochemical reaction is attached to said surfaces, for example, by covalent coupling, by interactions involving ligands, or by any other method for immobilizing this compound on the surface.

The microreactor according to the invention may have any shape, but it is advantageously substantially elongated in shape, the three zones described above being defined on a substantially flat substrate, the flow of fluid flowing substantially along the longitudinal axis of said reactor.

Advantageously, the means of the reaction zone, which confer on it a high surface-to-volume ratio, consist of blocks—or monoliths, as they are denoted in the prior art—comprising a base on said support connected to a top by means of a wall that is substantially perpendicular to the plane of said substrate, said blocks being evenly spaced out according to a two-dimensional network and defining, between their walls, channels connected to one another and substantially parallel to the longitudinal axis of the microreactor and flow axis of the flow of fluid.

Said blocks may have any shape, but advantageously their bases and their tops will have a shape chosen from discs, ellipses and polygons, preferably regular polygons, such as squares, diamonds, hexagons, etc.

The preferred shape for the base of the blocks or monoliths is that of a regular hexagon or else that of a square.

The size of these blocks is that, for example, of their base and/or top, for example in the form of a square or a regular hexagon, and it is defined by the fact that this base or top, preferably in the shape of a square or of a regular hexagon, can fit within a circle having a radius of 1 to 20 µm, preferably of 2 to 10 µm, for example of 5 µm.

Of course, different dimensions may be required by the applications and/or the nature of the products used.

Advantageously, said blocks are arranged in rows, the axis of which is substantially perpendicular to the longitudinal axis of the microreactor or flow axis of the flow of fluid, the blocks belonging to two successive rows being arranged in staggered rows, i.e. directly shifted.

Advantageously, the spacing between the axes of two successive rows is generally 10 to 30 µm, for example 12 µm, and the spacing between the centres of the bases of two blocks in the same row is 10 to 30 µm, for example 14 µm.

Of course, different dimensions may be required by the applications and/or the nature of the products used.

Advantageously, the means of the inlet zone, defined above, for giving the flow of fluid a constant flow rate, for evenly distributing the flow of fluid over the entire cross section of the reaction zone, and for increasing the surface-to-volume ratio as the flow of fluid progresses towards the reaction zone, consist of deflectors comprising a base on the support connected to a top by means of a wall that is substantially perpendicular to the plane of said substrate, said deflectors dividing the inlet channel into C channels, this division being repeated n times, such that the number of channels at the inlet of the reaction zone is equal to $C^n$, n and C being integers, and the total cross section of the channels at each division being constant and equal to the cross section of the inlet channel.

Preferably, C=2 or 3, more preferably C=2 and n is an integer from 2 to 10. The only limit for the number n is the selected size of the microreactor.

Advantageously, the means of the outlet zone for regrouping the flow of fluid derived from the reaction zone and for reducing the surface-to-volume ratio as the flow of fluid progresses from the reaction zone towards said outlet channel—said means being identical to the means provided in the inlet zone—consist of deflectors comprising a base on the support connected to a top by means of a wall that is substantially perpendicular to the plane of said substrate, said deflectors regrouping the channels of the reaction zone by dividing their number by S, this division being repeated m times, so as to form a single channel or outlet channel. S and m are integers, preferably S=2 or 3, more preferably S=2 and m is an integer from 2 to 10. The number m has the same limits as the number n.

Advantageously, the microreactor also comprises a cover or cap covering said inlet and outlet zones and said inlet and outlet channels.

The cover or cap is optionally provided with inlet and/or outlet orifices.

The invention also relates to a set of microreactors, as described above, formed on a substrate and comprising from 2 to 50 microreactors or more depending on the size of each of these microreactors.

Preferably, the microreactors of said set differ from one another by means of the shape of the blocks and/or the size of the blocks and/or their distribution (for example, space between the blocks and the rows) and/or their length.

The invention also relates to a system formed on a substrate and comprising at least one microreactor, as defined above, a fluid feed reservoir connected to said inlet or feed channel and a fluid outlet reservoir connected to said outlet channel.

According to one embodiment, the fluid feed reservoir is provided on the substrate on which the microreactor is formed, for example etched in the substrate, and the inlet channel is also provided on the substrate, for example etched in the substrate.

According to another embodiment, the fluid feed reservoir is placed outside the substrate on which the microreactor is formed, and the inlet channel—which connects the reservoir to the microreactor—is provided in the form of a capillary tube.

The same arrangements can be envisaged for the fluid outlet reservoir.

Advantageously, the microreactor, the system or the set, described above, may be connected to an analytical device, such as a mass spectrometer, preferably by means of a capillary leading to an "electrospray" or to a capillary electrophoresis device.

The invention also relates to a process for preparing a microreactor, as described above, said process comprising the following successive steps:

etching the three zones of the microreactor and, optionally, the inlet and outlet channels, in a substantially flat substrate;

covering, closing the microreactor by means of a cover or cap;

attaching a compound capable of producing a biological or chemical reactor to the surface of the reaction zone and, optionally, to the other surfaces of the microreactor.

Preferably, the etching is carried out by a process of isotropic or anisotropic dry etching.

Advantageously, the substrate is made of a material chosen from silica, oxidized silicon, silicon, polymers, plastics and resins, such as silicones, epoxy resins and elastomers.

Advantageously, said attachment is carried out by means of covalent coupling or by means of interactions involving ligands.

If the substrate is made of silica or of oxidized silicon and the compound to be attached is an enzyme, then the attachment is carried out by means of the series, sequence, of following steps:

rehydration in basic medium so as to obtain silanol sites;

silanization of the substrate with a reactive epoxy silane, such as 5,6-epoxyhexyltriethoxy-silane;

hydrolysis of the epoxide so as to give a diol;

oxidation of the diol to aldehyde;

immobilization of the enzyme, such as trypsin, by reaction of the amine functions of the lysine with the aldehydes;

optionally, reaction of the imine bonds thus formed, with a reducing agent.

Finally, the invention relates to a process for carrying out a biochemical or biological reaction, in which a flow of fluid is circulated in the microreactor, as described above, in order for at least one constituent of said flow of fluid to react with the compound capable of producing a biological or biochemical reaction, and a flow of fluid comprising the product(s) of said reaction is collected at the outlet of the microreactor.

Preferably, said reaction is a reaction of the enzyme/substrate type, said compound capable of producing a biological or biochemical reaction is an enzyme, said constituent of said flow of fluid is a substrate for the enzyme, and the product(s) of the reaction is (are) the product(s) derived from the reaction of said enzyme with said substrate.

The enzyme can be chosen from all enzymes, such as they have been defined above.

Preferably, said reaction is an enzymatic digestion reaction with a protease, said compound capable of producing a biological or biochemical reaction is a protease, said constituents of the flow of fluid are peptides or proteins, and the products of the reaction are peptide segments.

More preferably, the enzyme is trypsin.

The invention will now be described in detail in the description which follows, given by way of nonlimiting illustration, with reference to the attached drawings in which.

Figure 6:
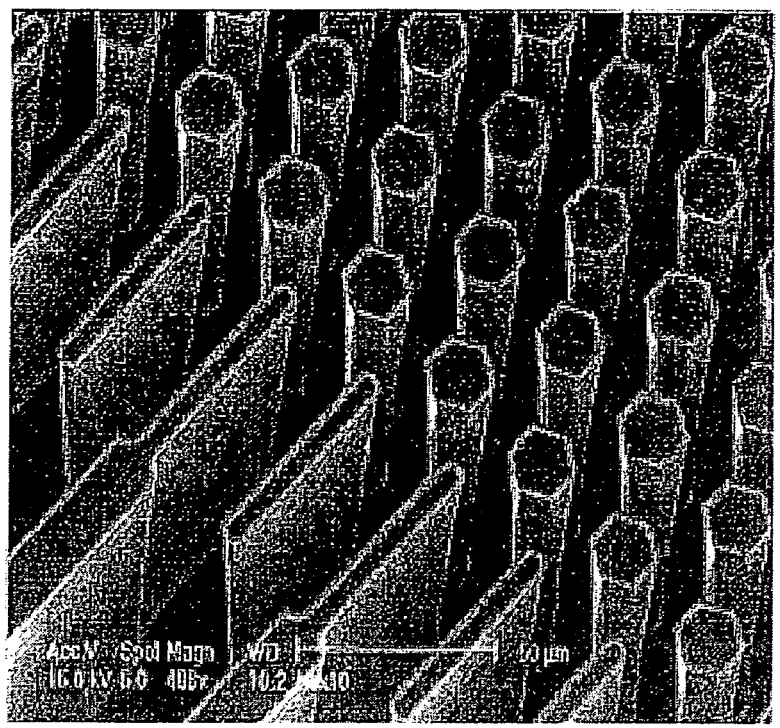
Figure 7:
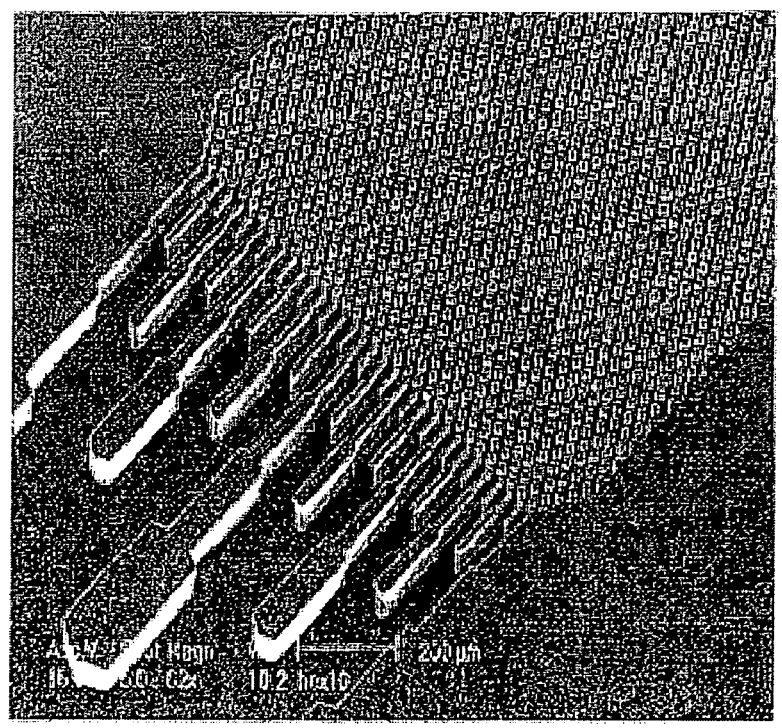

FIGS. 6 and 7 are photographs, taken on a scanning electron microscope, of a reactor produced according to the invention. In FIG. 6, the scale bar represents 200 μm; and in FIG. 7, the scale bar represents 50 μm.

Figure 1:
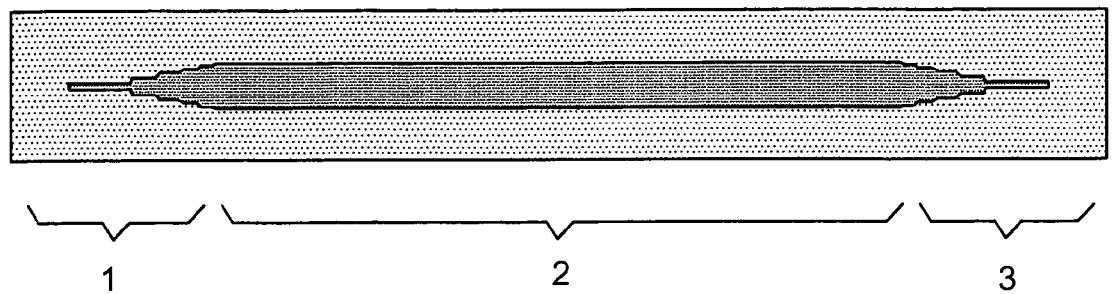
FIG. 1 is a sectional side view representing a general diagram of a microreactor according to the invention.

The microreactor according to the invention, the general diagram of which is illustrated in FIG. 1, comprises an inlet zone (1), a reaction zone (2) forming the "reactor" per se, and, finally, an outlet zone (3).

The microreactor shown diagrammatically in FIG. 1, has an elongated shape: this is the preferred form of the reactor, with a length, for example, of 10 to 30 mm, while its small dimension or width or diameter is, for example, from 0.5 mm to 1 mm, which justifies the term "microreactor". These dimensions are given by way of example and can be largely modified as needed.

It should be noted that the microreactor according to the invention may have, for example, the configuration of the column of document U.S. Pat. No. 6,156,273, mentioned above, but it is recalled that it differs fundamentally therefrom by the fact that it comprises a compound attached to its surfaces allowing a reaction, and that it is therefore a reactor and not a separation device.

The inlet zone (1) generally consists of a microchannel, followed by a system of zigzags arranged in the longitudinal direction of the microreactor. This system of zigzags or deflectors makes it possible to impose, for a fixed flow rate of the flow of fluid upstream of the microreactor, a constant rate of flow throughout the network of channels through the zigzags, before entering the main reactor. The network of channels also promotes a homogeneous distribution or dividing-up of the fluid so as to disperse it over the entire width of the reaction zone.

Finally, the dichotomic arrangement, for example, of the zigzags or deflectors makes it possible to increase the surface/volume ratio as the flow of fluid advances towards the core of the microreactor.

Figure 2:
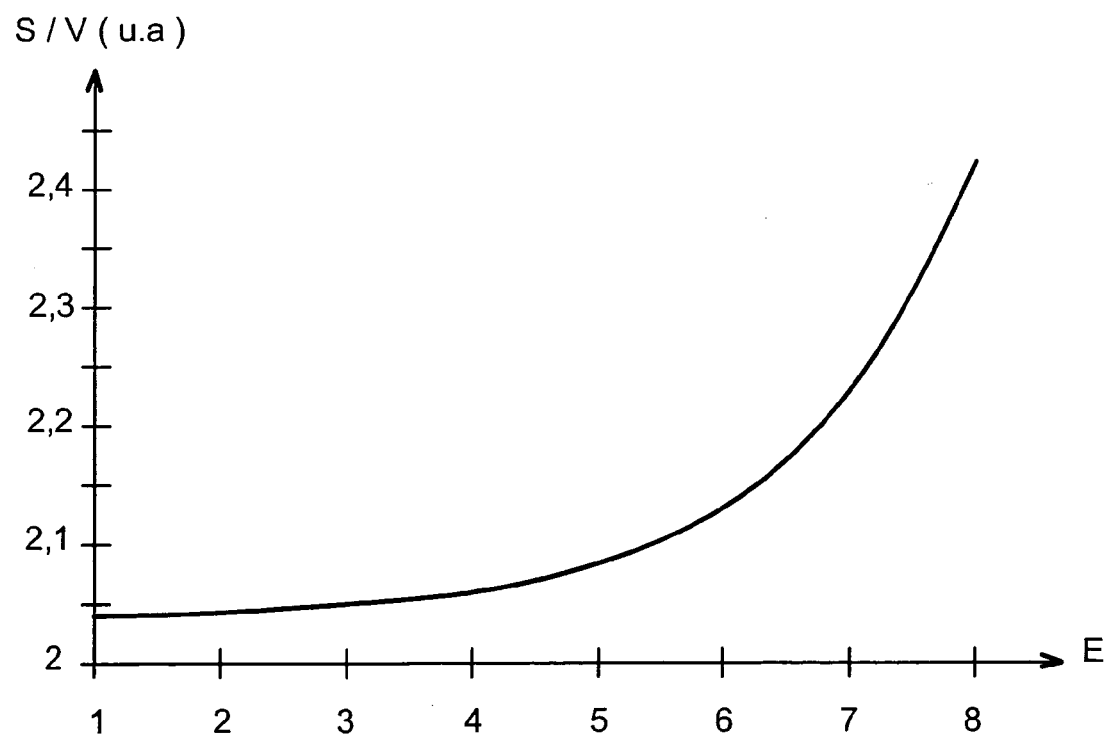
FIG. 2 is a graph which gives the surface/volume (S/V) ratio (in arbitrary units) for each stage (E) of the inlet of a microreactor, according to the invention.

FIG. 2, given by way of example, shows the surface to volume (S/V) ratio for each stage of the inlet of a microreactor according to the invention. It is noted that, the closer one gets to the start of the reaction zone (stage 8), the higher the surface/volume ratio.

The increase in the surface-to-volume ratio improves, as it goes along, the yield of the biological or biochemical reaction, until its optimum is reached in the core of the reactor, i.e. in the zone referred to as reaction zone.

The increase in surface is preferably provided by the presence of blocks that are substantially vertical on a substrate; these blocks may exhibit various geometries and also various sizes and various spacings, as is described later, in relation to FIG. 3. The length of the microreactor is also variable.

The length is generally fixed, in order to be able to optimize the yield of the reactor, for minimum obstruction, dimensions.

The outlet zone of the microreactor (3) is preferably identical in shape to the inlet; this part makes it possible in particular to regroup the various products derived from the biological reaction having taken place in the microreactor, i.e. essentially in the reaction zone (2), before subsequently using them, for example analysing them.

It is possible to integrate several microreactors on the same substrate, for example the same wafer, i.e. to form a set of microreactors on the same substrate.

Preferably, the microreactors that are on the same substrate will be different, the differences relating, for example, to the geometry of the blocks, making it possible to increase the surface-to-volume ratio and/or the spacing between blocks and/or the space between rows and/or the length of the reactor. The inlet of the reactor is only modified according to the size of the blocks selected.

Figure 3:
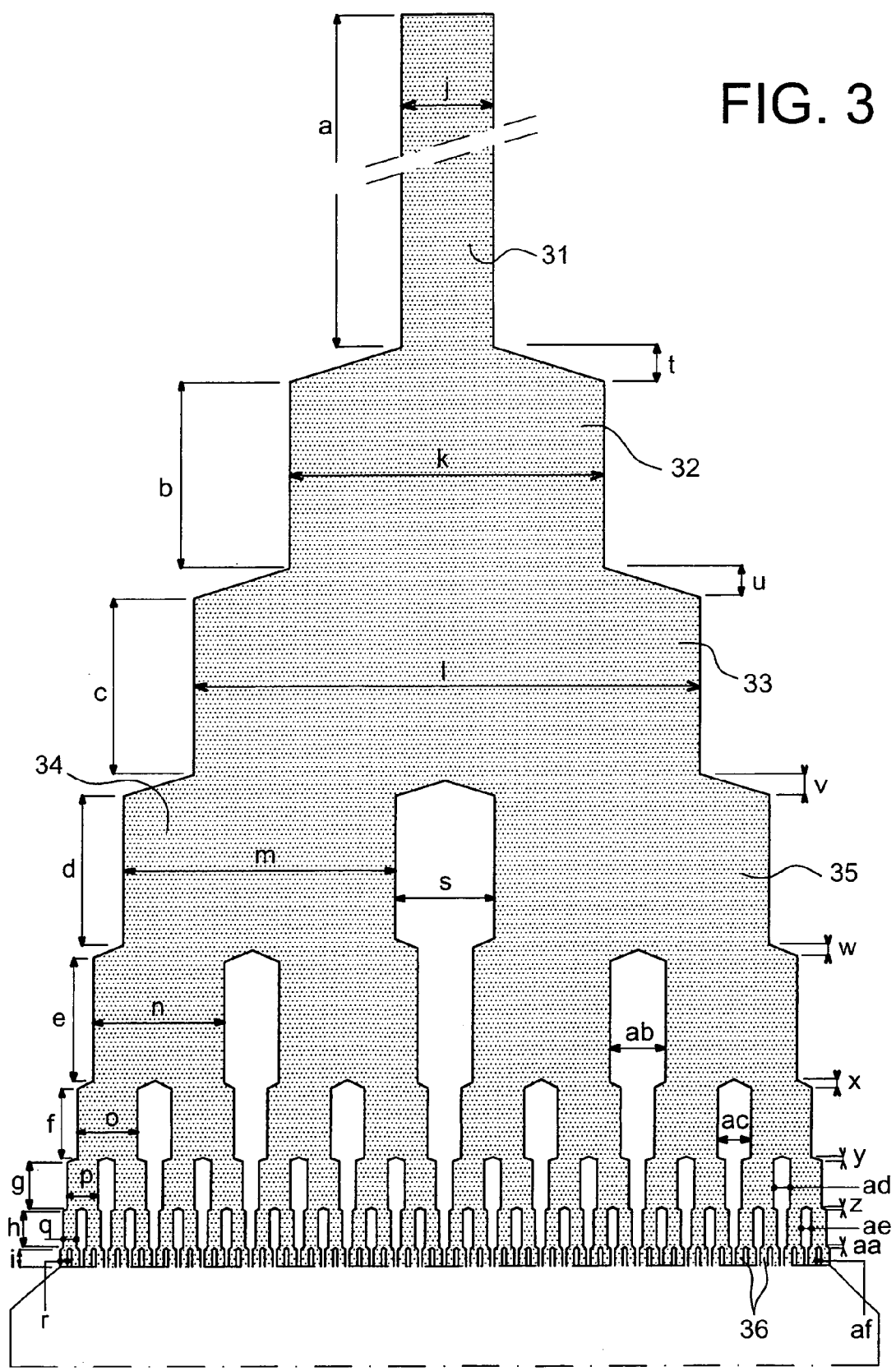
FIG. 3 is a view from above of the inlet and of the outlet of a microreactor according to the invention, prepared on a flat substrate.

FIG. 3 is a view from above of the inlet of the microreactor according to the invention, prepared on a flat substrate.

The microreactor is fed by means of a channel referred to as "microchannel" (31) having a width, for example, of 100 μm, which ends in a channel or distributor (32) having a width, for example, of 400 μm, and then, finally, in the first stage (33) of the inlet zone per se, which has a width of, for example, 640 μm.

The channel forming the first stage divides a first time into two channels (34) and (35), the widths of which are equal, namely: to 320 μm, and for which the sum of the widths is equal to that of the single channel (33).

In total, the single channel of the first stage is divided six times, each of the channels of a stage being divided into two channels of equal width and the total width of the channels of each stage being constant and always equal to the width of the channel of the first stage (640 μm). In the final stage of the inlet zone, there are sixty-four channels (36), and each one has a width, for example, of 10 μm.

The dimensions in microns of the microreactor inlet zone, illustrated in FIG. 1, have been indicated in Table I below, these dimensions being given only by way of example:

TABLE I

| Dimension | μm |
| --- | --- |
| a | 1500 |
| b | 350 |
| c | 300 |
| d | 250 |
| e | 200 |
| f | 150 |
| g | 100 |
| h | 50 |
| i | 25 |
| j | 100 |
| k | 400 |
| l | 640 |
| m | 320 |
| n | 160 |
| o | 80 |
| p | 40 |
| q | 20 |
| r | 10 |
| s | 128 |

TABLE I-continued

| Dimension | µm |
|---|---|
| t | 70 |
| u | 90 |
| v | 35 |
| w | 15 |
| x | 8 |
| y | 4 |
| z | 2 |
| aa | 1 |
| ab | 64 |
| ac | 32 |
| ad | 16 |
| ae | 8 |
| af | 4 |

FIG. 3 can represent both the inlet and the outlet of a microreactor according to the invention. For this, it is sufficient to reverse FIG. 3, the channel (31) then located at the bottom of the figure represents the outlet or evacuation channel.

Figure 4:
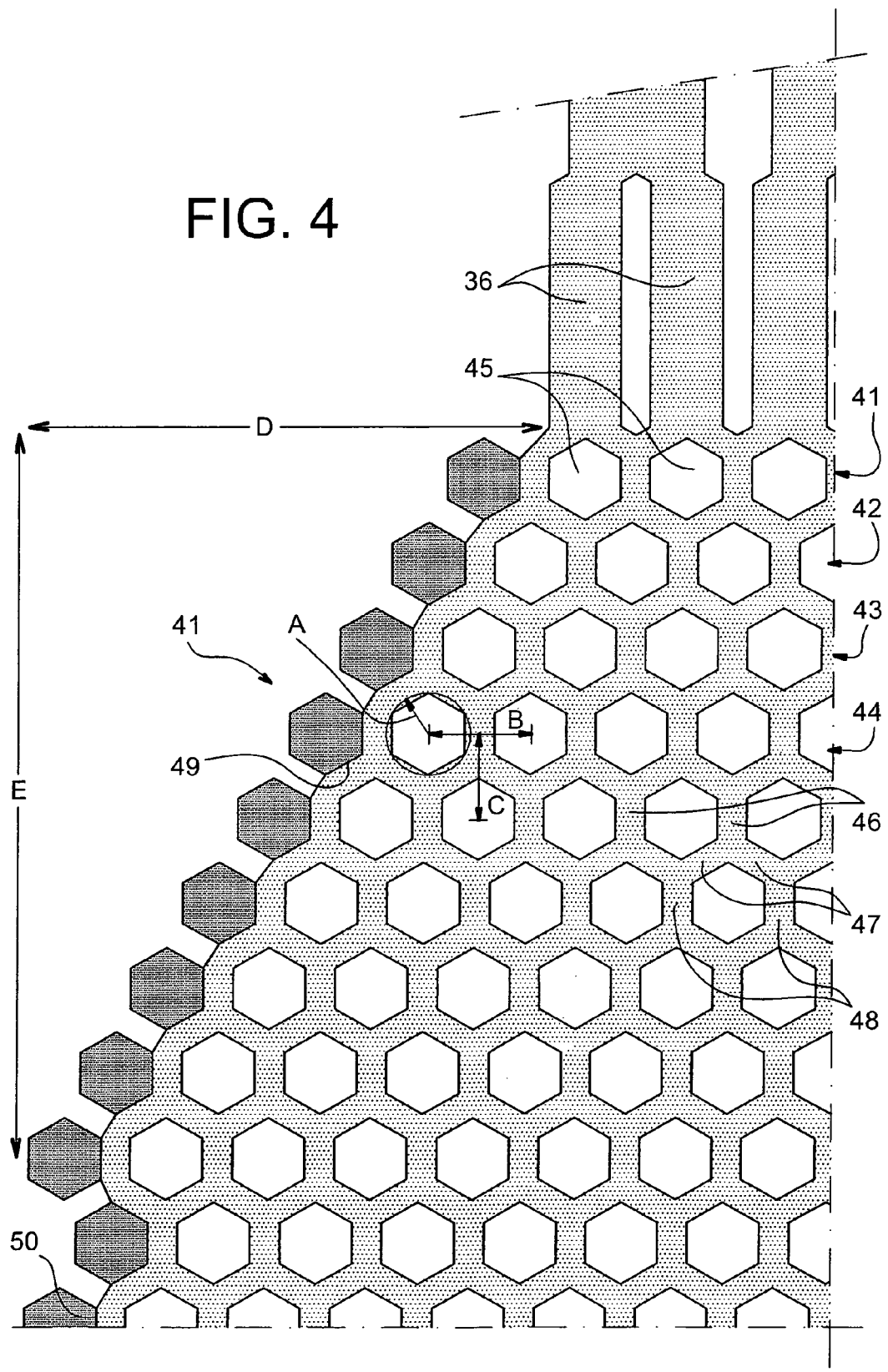
FIG. 4 is a view from above representing details of the inlet (and of the outlet) and of the edge of a microreactor according to the invention, and showing the arrangement and the designs of blocks of a microreactor according to the invention, these blocks having a base and a top in the shape of a regular hexagon.
Figure 5A:
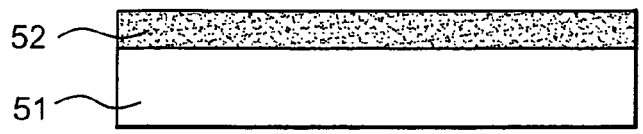
FIGS. 5A to 5F show the production of a microreactor according to the invention, in a substrate made of silicon, using essentially a process of photolithography.
Figure 5B:
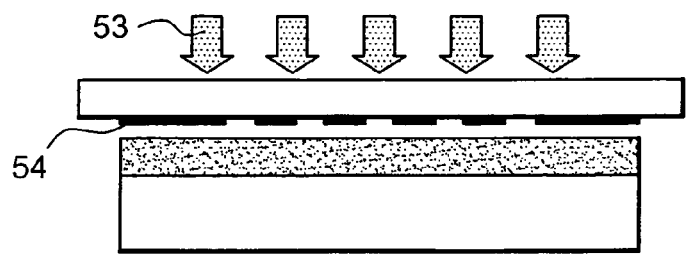
Figure 5C:
Figure 5D:
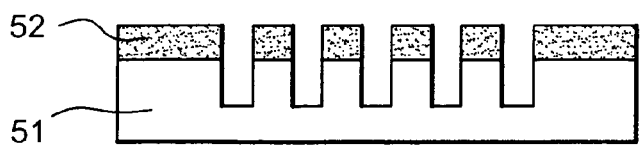
Figure 5E:
Figure 5F:

FIG. 4 represents the details of the inlet (and of the outlet) and of the edge of a microreactor according to the invention.

This figure shows the channels (36), already described above, which end in the reaction zone per se (41) of the microreactor according to the invention.

In this zone, blocks (45), etc., are arranged in parallel rows (41), (42), (43), (44), etc., and the axis of these rows is perpendicular to the longitudinal axis of the microreactor and to the flow axis of the flow of fluid.

In FIG. 4, the blocks have a base and a top in the shape of a regular hexagon, each of these hexagons fitting within a circle having a radius A, which is generally from 1 to 10 µm, for example 5 µm (by way of example).

The blocks of two successive rows are arranged in staggered rows and form, with one another, channels that are parallel to the direction of flow 46, which divide into channels 47, which then recombine as channels 48 that are once again parallel to the direction of flow.

In the same row, the centres of the blocks, for example of the hexagons, are 10 to 30 µm, for example 14 µm, apart (B) and the axes of two successive rows are generally from 10 to 30 µm, for example 12 µm, apart (C).

In FIG. 4, it is noted that the edge of the reaction zone again takes the outer shape of the blocks with the aim of maintaining a constant channel cross section and avoiding dispersion of the rate of flow of the fluid between the edges and the centre of the reactor.

The reaction zone opens out slowly from the inlet zone and the channels (36) by means of a tapered portion defined by the dimensions D and E, for example D=70 µm and E=10 µm, so as to end in the core or centre of the reaction zone limited by walls that are essentially parallel, one (50) of which is represented in FIG. 4.

The reaction zone provides virtually all the biological function of the microreactor.

The increase in surface is precisely provided by the presence of the blocks which can, besides the hexagonal geometry represented in the figure, have other geometries, for example the blocks may be in the form of a diamond, an ellipse or a disc, and may also have a different size and spacing (distance between two blocks), for example of 10 to 30 µm.

Preferably, a cross section that is either hexagonal, as in FIG. 4, or square, which fits within a circle of variable diameter, for example of 2 to 20 µm, is used, in order to obtain a compromise between a maximum surface area, defining a network of interconnected microchannels that are virtually parallel to the longitudinal axis of the microreactor (the presence of channels perpendicular to the longitudinal axis would induce product stagnation and would decrease the yield of the microreactor) and minimizing the complexity of the technological implementation.

As was indicated above, the outlet zone is generally symmetrical to the inlet zone.

The microreactor according to the invention can be produced for any suitable process, but when it is prepared on or in an essentially flat substrate, the microreactor may be, for example, prepared by anisotropic (or isotropic) dry etching in silicon using, for example, a process of the ICP-DRIE (inductively coupled plasma, deep reactive ion etching) type.

The units—the term "unit" is intended to mean the feed and evacuation channels, the inlet, reaction and outlet zones, formed for example by the deflectors and blocks—are then defined in the silicon by an etching mask, for example by a photoresist, commonly used in microelectronics or, for example, by silica, this mask being sufficiently thick to allow the features to be etched in the silicon, at the thickness chosen by the operator, for example from 50 µm to 100 µm.

The features can be defined in this etching mask, for example, by a lithography process conventionally encountered in microelectronics, followed, for example in the case of silica, by reactive ion etching of this material.

The reactors may also be, for example, prepared by anisotropic dry etching in silica, it being possible for the selected protective mask to then be, for example silicon. The microreactor may also be prepared in other materials, for example made of polymers, such as epoxy resins, elastomers, plastics.

The use of microtechnology makes it possible to produce, by means of anisotropic or isotropic etching, structures that have complex geometries and very large surface-to-volume ratios, without the drawbacks of microbead fillings.

The reactor can then be covered, for example with a PDMS (polydimethylsiloxane) sheet, which may or may not comprise inlet and/or outlet orifices, after treatment of said cover and of the reactor with an oxygen plasma, as described in the literature. In this case, PDMS is known to have properties of spontaneous adhesion on most solid supports.

The reactor may also, for example, be covered by molecular bonding of a silica plate or of a glass plate, which may or may not comprise inlet and/or outlet orifices, after cleaning and chemical preparation of the two hydroxylated substrates (substrate $SiO_2$ on silicon/glass or silica cover). The presence of silanol sites (SiOH) at the surface spontaneously attracts water molecules, and the two parts of the microcomponent, namely: cover and reactor, bond to one another via water molecules. Some of the water contained between the two surfaces is eliminated by heating, until about three layers of water molecules which make the adhesion possible are obtained.

Alternatively, the microreactor may be, for example, covered by anodic bonding of a glass plate, which may or may not comprise inlet and/or outlet orifices.

Alternatively, the microreactor may, for example, be covered by bonding of a polymer plate chosen by the user, which may or may not compromise inlet and/or outlet orifices, using for example a screen-printing adhesive coating process.

This type of bonding consists of three main steps: screen printing, which consists in applying adhesive only to certain zones of the substrate, bonding, which consists in bringing the substrate locally coated with adhesive into contact with the cover and, finally, heating, which induces polymerization of the adhesive. The curing can be carried out photochemically if the adhesive is UV-polymerizable.

Finally, the microreactor may be, for example, covered by SDB (silicon direct bonding) to a silicon plate, which may or may not comprise inlet and/or outlet orifices.

The attachment of the constituent having the biological or biochemical function in the microreactor, which may be for example an enzyme of the trypsin type, can be carried out according to various methods:
by means of covalent coupling linking the molecule to be attached to the surface of the microreactor;
by means of interactions involving ligands.

Thus, in the case of an enzyme such as trypsin, the attachment thereof to a silica substrate can be carried out by means of successive steps of rehydration, silanization, for example with a reactive epoxy silane, hydrolysis, oxidation and, finally, immobilization, attachment of the enzyme via —NH$_2$ bonds carried by the lysine groups of the trypsin.

Scheme 1 below illustrates the steps and the operating conditions which can be used to immobilize an enzyme such as trypsin.

SCHEME 1

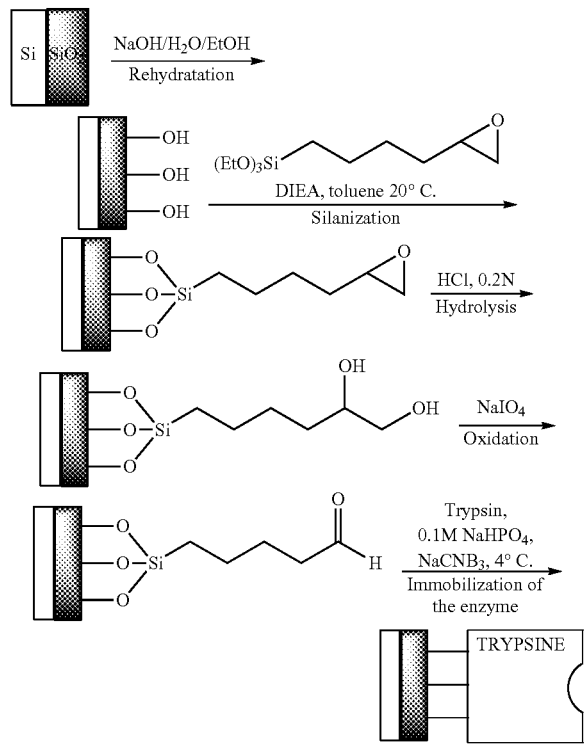

By way of indication, trypsin carrying a biotin function (biotinylated trypsin, type XI-B from SIGMA ALDRICH®) was attached to circular surfaces of the order of 1 mm in diameter.

After a step consisting in labelling with streptavidin carrying a Cy$_3$ fluorophore, and excitation at 550 nm, a fluorescence image is obtained at 580 nm, the intensity of which is 225 AU (arbitrary units). The signal/noise (trypsin/substrate) ratio is between 35 and 40.

To carry out a reaction inside the microreactor according to the invention, the flow of liquid of which one of the constituents can react with the compound attached to the walls of the microreactor is passed through using an appropriate device, such as a syringe pump and its associated syringe, or the like. The flow rate is preferably a constant flow rate, which ensures that the amount of time spent inside the reactor is from 1 to 15 minutes, for example as a function of the kinetics of the reaction in the microreactor. The products of the reaction are sent towards an analytical device, such as a mass spectrometer, or towards another use, for example a capillary electrophoresis.

The invention will now be described with reference to the following examples, given by way of non-limiting illustration.

EXAMPLES

Example 1

This example illustrates the production of a silicon microreactor, with reference to the attached FIG. 5.

A layer of photoresist (52) of the SHIPLEY® S 1813 type is deposited by spin-coating onto a four-inch (10.16 cm) silicon substrate (51) of <100> type and of thickness 525 μm.

Lithography is then performed by means of a UV exposing beam (53) through a mask (54) provided with or having n features defining the geometry of the microreactors; the exposure time is 10 seconds.

This pattern is subjected to deoxidation of the pattern bottoms by means of a Nextral NE 110 RIE device in a CHF$_3$/O$_2$ atmosphere at a flow rate ratio of 50/10 sccm, under a pressure of 100 mT, with a power of 10 W, for 1 minute.

Next, the zones not protected by the resin are etched using a deep etching device of the Multiple STS ICI DRIE type.

The following step consists in cutting the mask of resin with fuming HNO$_3$ without ultrasound for 5 minutes.

The sidewalls of the etched patterns are then cleaned by oxidation in a tube furnace in oxygen for 50 minutes at 1000° C. and chemical deoxidation with HF for a few seconds.

Thick oxidation of the patterns over a thickness of 3 μm (55) is then carried out in a tube furnace under steam at 1000° C. for 18 hours and 50 minutes.

Each microreactor is then cut out and separated from the wafer. A polydimethylsiloxane cover is then used to close the microreactor. The bonding of the cover and of the microreactor is carried out after oxygen plasma treatment of the two surfaces to be brought into contact (TEGAL O$_2$ plasma device, pressure 100 mTorr, activation time 30 seconds). The microreactor is connected with any device for circulating fluid, via capillaries inserted into the inlet and outlet channels of the microreactor.

The microreactor used in the digestion example has a hexagonal block geometry with blocks that are 10 microns in diameter, separated from one another by 14 microns along an axis perpendicular to the direction of the flow of liquid, and by 12 microns along an axis parallel to the flow of the liquid. The depth of the microreactor, defined as being the average height of the blocks, is 50 microns.

Example 2

In this example, trypsin is attached, immobilized on the surfaces of the microreactor produced in Example 1, so as to obtain a "functionalized" microreactor according to the invention.

The immobilization of the trypsin is then verified by fluorescence.

The trypsin used is a type I trypsin from bovine pancreas, sold by the company SIGMA ALORICA® (ref. T 8003).

The reaction mechanism is composed of several steps, namely:

rehydration in basic medium making it possible to obtain silanol sites, silanization of the substrate with 5,6-epoxyhexyltriethoxysilane resulting in the formation of films;

hydrolysis so as to convert the epoxide function into a diol function;

oxidation to an aldehyde function and, finally, immobilization of the enzyme by reaction of the amine functions carried by the lysines, with the aldehyde functions. The imine bonds thus formed are stabilized by reaction with a reducing agent. The precise protocol used in this example is described below.

1. Rehydration

| NaOH Brown: | NaO | 4.9 g; |
|---|---|---|
| | EDI | 14.7 ml; |
| | EtOH | 19.6 ml; | filling of the microreactor at 3 µl/m, reaction for 2 hours at ambient temperature. Emptying of the reactor under a stream of nitrogen, then washing with deionized water (100 µl at 3 µl/min). Oven for 15 minutes at 80° C. Rinsing with toluene (50 µl at 3 µl/min).

2. Silanization

Toluene 10 ml;
DIEA 50 µl;
5,6-Epoxyhexyltriethoxysilane 25 µl;
filling of the microreactor at 3 µl/min, and then washing with ethanol (100 µl at 3 µl/min);
crosslinking for 3 hours at 110° C.

3. Hydrolysis 0.2N HCl. Filling of the reactor at 3 µl/min. Reaction under a stream of HCl for 3 hours at ambient temperature. Emptying, then washing with deionized water (100 µl at 3 µl/min).

Drying for 30 minutes at 110° C.

4. Oxidation $NaIO_4$ 6.6 µg;
Deionized water 3 ml.

Reaction under a stream of said reactants (100 µl at 3 µl) for 1 hour at ambient temperature. Emptying and drying under a stream of nitrogen.

5. Immobilization of the Enzyme

The solution containing the enzyme to be immobilized is introduced into the microreactor at a fixed flow rate. Once the microreactor is full, its ends are blocked off with parafilm. The immobilization reaction is then carried out in static mode.

Using this reaction scheme and the associated protocol, biotinylated trypsin (biotinylated trypsin type XI-B from SIGMA ALDRICH® provided in the form of a solution of 2.5 mg/ml of trypsin, 0.1M $Na_2HPO_4$, 0.05 M $NaCNBH_3$) was immobilized on the internal surface of the microreactor exhibiting columns 10 µm in diameter, 5 µm apart, and equal to 50 µm in height, and then visualised with a solution of streptavidin $Cy_3$.

The biotin/streptavidin-$Cy_3$ couple is visualised by fluorescence at 570 nm.

Observation under an epifluorescent microscope makes it possible to visualise the presence of trypsin over the entire surface of the microcolumns and over the entire tryptic reactor.

Example 4

In this example, digestion of BSA is carried out in the microreactor provided with an immobilized enzyme, according to the invention, prepared in Example 3.

By means of a syringe pump, the inlet reservoir of the microreactor is filled with a solution of bovine serum albumin (BSA) at 2 mg/ml with 0.05% of $NaN_3$, at an average flow rate of the order of 5 µl/min. The amount of time spent in the microreactor by the protein to be digested is of the order of 5 minutes. After a few minutes, the volume infused through the microreactor is sufficiently large to allow correct analysis on a MALDI_TOF mass spectrometer. The spectrum obtained shows peptide segments derived from the digestion of the BSA.

REFERENCES

[1] P. D. I. FLETCHER, S. J. HASWELL, V. N. PAUNOV, Analyst 124, 1273-1282 (1999)

[2] T. McCREEDY, Analytica Chimica Acta 427, 39-43 (2001)

[3] B. He, H. TAIT, F. REGNIER, Analytical Chemistry 70, 3790-3797 (1998)

[4] B. He, L. TAN, F. REGNIER, Analytical Chemistry 71, 1464-1468 (1999)

[5] B. He, J. Ji, F. REGNIER, Journal of Chromatography A 853, 257-262 (1999)

[6] B. He, B. J. BURKE, X. ZHANG, R. ZHANG, F. REGNIER (Website of Analytical Chemistry, 2000)

[7] B. E. SLENTZ, N. A. PENNER, F. REGNIER, Journal of Chromatography A, to be published not yet communicated (2001)

[8] L. XIONG, F. REGNIER, Journal of Chromatography A 924, 165-176 (2001)

[9] Chemical Abstracts 2001: 335 569, MIYAZAKI M. et al. Chem. Lett. (2001), (5), 442-443

[10] Chemical Abstracts 2000: 811 299 CAPLUS

The invention claimed is:

1. A microreactor substantially elongated in shape and formed on a substantially flat substrate comprising:
   (i) an inlet or feed channel having deflectors dividing the inlet channel into 2 to 10 channels,
   (ii) an inlet or feed zone for a flow of fluid,
   (iii) an active zone comprising means which confer on it a high surface-to-volume ratio consisting of blocks comprising a base on a support connected to a top via a wall that is substantially perpendicular to the plane of said substrate, said blocks being evenly spaced out by 10 to 30 µm between the axes of two successive rows according to a two-dimensional network and defining, between the walls, channels connected to one another and substantially parallel to the longitudinal axis of the microreactor and flow axis, and said blocks having a base or top that can fit within a circle of 1 to 20 µm,
   (iv) an outlet zone and an outlet or evacuation channel having deflectors dividing the outlet channel into 2 to 10 channels, said zones and channels being in fluid communication in which the flow of fluid is substantially along the longitudinal axis of said reactor, wherein the active zone is a reaction zone comprising at least one enzyme capable of producing a biological or biochemical reaction with at least one substrate for said enzyme, said at least one enzyme being attached to the surfaces of said reaction zone whereby said at least one enzyme reacts with said at least one substrate to create a new compound having a different chemical structure as a reaction product, wherein said reaction product may be obtained at the outlet channel of the microreactor, and wherein said enzyme is chosen from the oxidoreductase class, the lyase class, the isomerase class, or the ligase or synthetase class.

2. A microreactor according to claim 1, wherein:
said inlet zone comprises means for giving said flow of fluid a constant flow rate, for evenly distributing the flow of fluid over the entire cross section of said reaction zone, and for increasing the surface/volume ratio as the flow of fluid progresses towards the active zone which is a reaction zone said at least one enzyme capable of producing a biological or biochemical reaction with at least one substrate for said enzyme is attached to the surfaces of said inlet zones, active zone which is a reaction zone, and outlet zone;

said outlet zone comprises means for regrouping the flow of fluid derived from the active zone which is a reaction zone comprising the products derived from said biological or biochemical reaction, and for reducing the surface-to-volume ratio as the flow of fluid progresses from the active zone which is a reaction zone towards said outlet channel, and for evacuating said flow of fluid.

3. A microreactor according to claim 1, wherein the largest dimension of said microreactor is from 10 mm to 30 mm.

4. A microreactor according to claim 1 wherein the enzyme is an enzyme with lytic activity, or an enzyme having an activity that modifies or acts on nucleic acids.

5. A microreactor according to claim 1, wherein the protease is chosen from endopeptidases and exopeptidases.

6. A microreactor according to claim 1, wherein the enzyme is trypsin and the substrate for this enzyme is a peptide or a protein.

7. A microreactor according to claim 1, wherein the compound capable of producing a biological or biochemical reaction is attached to said surfaces by means of covalent coupling or by means of interactions involving ligands.

8. A microreactor according to claim 1, wherein the base and the top of said blocks have a shape chosen from ellipses, discs and polygons.

9. A microreactor according to claim 1, wherein the blocks have a base and a top in the shape of a regular hexagon.

10. A microreactor according to claim 1, wherein the blocks have a base in the form of a square.

11. A microreactor according to claim 1, wherein the base and the top of said blocks can fit within circles having a radius of 1 to 20 µm.

12. A microreactor according to claim 1, wherein said blocks are arranged in rows, the axis of which is substantially perpendicular to the longitudinal axis of the microreactor or flow axis, the blocks belonging to two successive rows being arranged in staggered rows.

13. A microreactor according to claim 12, wherein the spacing between the axes of two successive rows is 10 to 30 µm, and the spacing between the centers of the bases of two blocks in the same row is 10 to 30 µm.

14. A microreactor according to claim 1, wherein the means of the inlet zone for giving the flow of fluid a constant flow rate, for evenly distributing the flow of fluid over the entire cross section of the reaction zone, and for increasing the surface-to-volume ratio as the flow of fluid progresses towards the reaction zone, consist of deflectors comprising a base on the support connected to a top by means of a wall that is substantially perpendicular to the plane of said substrate, said deflectors dividing the inlet channel into C channels, this division being repeated n times, such that the number of channels at the inlet of the reaction zone is equal to $C^n$, n and C being integers, and the total cross section of the channels at each division being constant and equal to the cross section of the inlet channel.

15. A microreactor according to claim 14, wherein C=2 or 3 and n is an integer from 2 to 10.

16. A microreactor according to claim 1, wherein the means of the outlet zone for regrouping the flow of fluid derived from the reaction zone and for reducing the surface-to-volume ratio as the flow of fluid progresses from the reaction zone towards said outlet channel, said means being identical to the means provided in the inlet zone, consist of deflectors comprising a base on the support connected to a top by means of a wall that is substantially perpendicular to the plane of said substrate, said deflectors regrouping the channels of the reaction zone by dividing their number by S, this division being repeated m times, so as to form a single channel or outlet channel.

17. A microreactor according to claim 1, also comprising a cap or cover covering said zones and said channels, optionally provided with inlet and/or outlet orifices.

18. A set of microreactors according to claim 1, formed on a substrate and comprising from 2 to 50 microreactors.

19. A set of microreactors, said microreactors according to claim 18 wherein said microreactors differ from one another by means of the shape of the blocks and/or the size of the blocks and/or their distribution and/or the length of the microreactor.

20. A system formed on a substrate and comprising at least one microreactor according to claim 1, a fluid feed reservoir connected to said inlet or feed channel, and a fluid outlet reservoir connected to said outlet channel.

21. A system according to claim 20, wherein the fluid feed reservoir is provided on the substrate on which the microreactor is formed, and the inlet channel is also provided on the substrate.

22. A system according to claim 20, wherein the fluid feed reservoir is placed outside the substrate on which the microreactor is formed, and the inlet channel is provided in the form of a capillary tube.

23. A process for preparing a microreactor according to claim 1, said process comprising the following successive steps:
etching the three zones of the microreactor and, optionally, the inlet and outlet channels, in a substantially flat substrate;
covering, closing the microreactor by means of a cover or cap;
attaching a compound capable of producing a biological or chemical reactor to the surfaces of the reaction zone and, optionally, to the other surfaces of the microreactor.

24. A process according to claim 23, wherein the etching is carried out by a process of isotropic or anisotropic dry etching.

25. A process according to claim 23, wherein the substrate is made of a material chosen from silica, silicon, oxidized silicon, polymers, plastics and resins.

26. A process according to claim 23, wherein said attachment is carried out by means of covalent coupling or by means of interactions involving ligands.

27. A process according to claim 23, wherein the substrate is made of silica or of oxidized silicon and the compound to be attached is an enzyme, and the attachment is carried out by means of the following succession of steps:
rehydration in basic medium so as to obtain silanol sites;
silanization of the substrate with a reactive epoxy silane;
hydrolysis of the epoxide so as to give a diol;
oxidation of the diol to aldehyde;

immobilization of the enzyme by reaction of the amine functions with the aldehydes;

optionally, reaction of the imine bonds thus formed, with a reducing agent.

28. A process for carrying out a biochemical or biological reaction, wherein a flow of fluid is circulated in a microreactor according to claim 1, in order for at least one substrate to react with the enzyme capable of producing a biological or biochemical reaction, and a flow of fluid comprising the product(s) of said reaction is collected at the outlet of the microreactor.

29. A process according to claim 28, wherein said reaction is an enzymatic digestion reaction with a protease, said enzyme capable of producing a biological or biochemical reaction is a protease, and said substrate is a peptide or a protein, and the products of the reaction are peptide segments.

30. A process according to claim 29, wherein the enzyme is trypsin.

31. A microreactor according to claim 4, wherein the enzyme with lytic activity is a protease, a nuclease, a lipase, a glycolase, or a kinase.

32. A microreactor according to claim 4, wherein the enzyme having an activity that modifies or acts on nucleic acids is DNA or RNA polymerase, primase, DNA ligase, a nuclease, a reverse transcriptase, a kinase, a phosphatase, a phosphorylase, a restriction endonuclease, a topoisomerase or a transferase.

33. A microreactor according to claim 5, wherein the endopeptidases are chosen from pepsin, trypsin, chymotrypsin, cathepsin A, cathepsin B and cathepsin C, and the exopeptidases are chosen from carbopeptidases, aminopeptidases and dipeptidases.

34. A microreactor according to claim 8, wherein the base and the top of said blocks have a shape chosen from regular polygons.

35. A microreactor according to claim 34, wherein the regular polygons are diamonds, squares or hexagons.

36. A microreactor according to claim 11, wherein the base and the top of said blocks are in the form of squares or of regular hexagons.

37. A microreactor according to claim 11, wherein the base and the top of said blocks can fit within circles having a radius of 2 to 10 µm.

38. A process according to claim 23, wherein the substrate is made of a material chosen from silicones, epoxy resins and elastomers.

39. A microreactor according to claim 1, wherein the compound capable of producing a biological or biochemical reaction is attached to said surfaces by means of covalent coupling.

* * * * *